United States Patent [19]

Menapace

[11] Patent Number: 4,484,006

[45] Date of Patent: Nov. 20, 1984

[54] SYNTHESIS OF 2-METHYLBUTANAL

[75] Inventor: Henry R. Menapace, Stow, Ohio

[73] Assignee: The Goodyear Tire & Rubber Company, Akron, Ohio

[21] Appl. No.: 502,877

[22] Filed: Jun. 9, 1983

[51] Int. Cl.$^3$ .............................................. C07C 45/50
[52] U.S. Cl. ..................................... 568/454; 568/909
[58] Field of Search ........................ 568/454, 451, 909

[56] References Cited

U.S. PATENT DOCUMENTS

| | | | |
|---|---|---|---|
| 3,150,188 | 9/1964 | Eisemmann et al. | 568/454 |
| 3,515,757 | 6/1970 | Sibert | 568/454 |
| 3,937,742 | 2/1976 | Yoo | 568/454 |
| 3,965,192 | 7/1976 | Booth | 568/454 |
| 3,976,596 | 8/1976 | Hawthorne et al. | 568/454 |
| 3,989,759 | 11/1976 | Yoo | 568/454 |
| 3,991,119 | 11/1976 | Yoo | 568/454 |
| 4,012,450 | 3/1977 | Bond | 568/454 |
| 4,258,215 | 3/1981 | Dawes | 568/454 |
| 4,400,547 | 8/1983 | Dawes | 568/454 |
| 4,400,549 | 8/1983 | Richter et al. | 568/454 |

FOREIGN PATENT DOCUMENTS 0080449  6/1983  European Pat. Off. ............ 568/454

*Primary Examiner*—Werren B. Lone
*Attorney, Agent, or Firm*—Alvin T. Rockhill

[57] ABSTRACT

This invention reveals a process for the synthesis of 2-methylbutanal (2-methylbutyraldehyde). 2-methylbutanal is a chemical intermediate that is useful in the synthesis of isoprene (2-methyl-1,3-butadiene). In utilizing the process of this invention 2-butene is hydroformylated into 2-methylbutanal with only a minimal amount of n-pentanal being produced as a by-product. More specifically, this invention reveals a process for the synthesis of 2-methylbutanal from 2-butene comprising: hydroformylating 2-butene with a catalyst selected from the group consisting of hydridocarbonyltris (triphenylphosphine) cobalt, hydridocarbonyltris (triphenylphosphine) rhodium, and hydridocarbonyltris (triphenylphosphine) iridium in the presence of hydrogen and carbon monoxide wherein said hydroformylation is carried out in the presence of excess triphenylphosphine.

6 Claims, No Drawings

SYNTHESIS OF 2-METHYLBUTANAL

BACKGROUND OF THE INVENTION 2-methylbutanal (2-methylbutyraldehyde) is a chemical intermediate that is useful in the synthesis of isoprene (2-methyl-1,3-butadiene). Isoprene is in turn useful as a monomer in the synthesis of synthetic rubber.

Hydroformylation reactions, commercially known as the oxo process, were discovered by O. Roelin in Germany and patented in 1943 (see U.S. Pat. No. 2,327,066). Hydroformylation is the addition of hydrogen and carbon monoxide to an alkene to form an aldehyde which can be further reduced to an alcohol. Hydroformylation reactions are carried out in the liquid phase in the presence of transition-metal catalysts. For example, olefins can be hydroformylated into aldehyde by treatment with carbon monoxide and hydrogen in the presence of a transition metal catalyst (cobalt carbonyl), as is shown below.

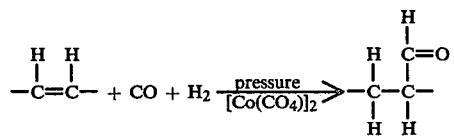

Alcohol can be obtained by allowing this reaction to continue after all the carbon monoxide (CO) is used up, see the reaction shown below.

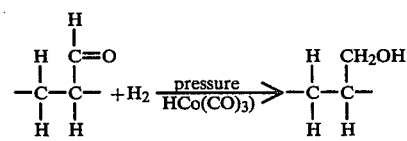

In light of this hydroformylation chemistry the synthesis of pure 2-methylbutanal would appear to be quite simple. However, in practice the synthesis of relatively pure 2-methylbutanal from 2-butene cannot be achieved by employing standard oxo processes. The problem encountered is that attempts to hydroformylate 2-butene into 2-methylbutanal result in the formation of n-pentanal as well as 2-methylbutanal. Thus, mixtures of 2-methylbutanal and n-pentanal are produced in lieu of pure 2-methylbutanal. The hydroformylation of 2-butene can result in the formation of mixtures containing over 25 weight percent n-pentanal unless the techniques of this invention are employed.

Many transition-metal ions and complexes, especially of Group VIII metals promote double bond migration in alkenes. Thus, a possible explanation for the formation of n-pentanal is that 2-butene is isomerized into 1-butene in the presence of transition-metal hydroformylation catalysts with the 1-butene then being hydroformylated into n-pentanal and 2-methylbutanal. In other words, it is theorized that 2-butene is isomerized into 1-butene under the conditions employed in an oxo process with the 1-butene then being hydroformylated into a mixture of normal-pentanal and 2-methybutanal. The reaction scheme shown below as FIG. 1 illustrates three possible reaction paths that can be taken in the hydroformylation of 2butene.

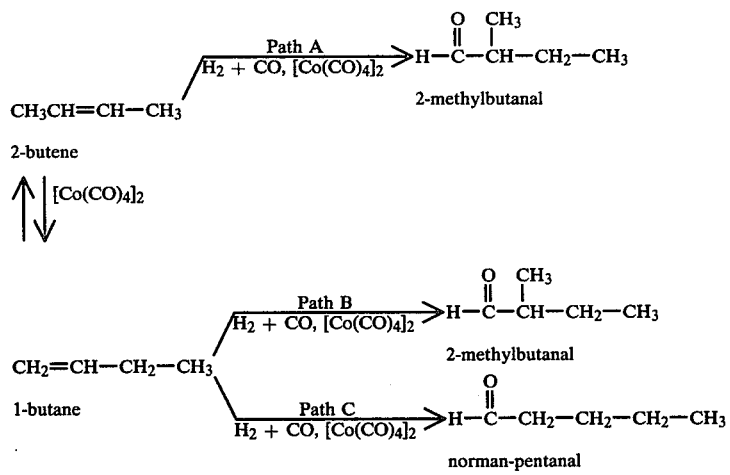

FIG. 1

As can clearly be seen, if 2butene is hydroformylated, as is shown as Path A, then the only possible reaction product is 2-methylbutanal. In the presence of the transition-metal catalysts used in hydroformylation reactions 2-butene can isomerize into 1-butene as is shown in the reaction scheme, thus making Path B and Path C possible. If Markownikoff addition is followed, as illustrated in Path B, then a branched-chain product will be produced (2-methylbutanal). On the other hand, if anti-Markownikoff addition is followed as illustrated in Path C, then a straight-chain product (normal-pentanal) will be formed. The hydroformylation of 1-butene normally produces both the straight- and branched-chain products. Normally in a hydroformylation reaction of this type one would expect to observe a ratio of straight-chain products to branched-chain products of about 3:1. In other words, anti-Markownikoff addition is favored over Markownikoff addition by a 3:1 margin. Thus, Path C is preferred to Path B by about 3:1. Therefore, the hydroformylation of 1-butene will normally result in the formation of about 75 percent n-pentanal and 25 percent 2-methylbutanal. The literature indicates that this ratio of straight-chain (normal) to branched chain products can be shifted to favor straight-chain product by an even greater margin if the hydroformylation is done in the presence of high concentrations of triphenylphosphine, see C. U. Pittman & A. Hirao, Journal of Organic Chemistry, Vol. 43, No. 4, p. 640 (1978).

In order for the oxo process to be used on a commercial basis for synthesizing 2-methylbutanal from 2-butene it is most important to inhibit reaction Path C. This is because it is highly undesirable to produce n-pentanal in the hydroformylation of 2-butene which is intended to produce 2-methylbutanal. By practicing the process of this invention the amount of n-pentanal produced in the hydroformylation of 2butene can be greatly reduced. Thus, this invention allows for the hydroformylation of 2-butene to provide 2-methylbutanal that contains a relatively small amount of n-pentanal.

SUMMARY OF THE INVENTION

The hydroformylation of 2-butene normally results in the formation of a mixture of 2-butanal and n-pentanal. However, by utilizing the hydroformylation process of this invention 2-butene can be hydroformylated into 2-methylbutanal which contains only a minimal amount of n-pentanal. More specifically, this invention reveals a process for the synthesis of 2-methylbutanal from 2-butene comprising: hydroformylating 2-butene with a catalyst selected from the group consisting of hydridocarbonyltris (triphenylphosphine) cobalt, hydridocarbonyltris (triphenylphosphine) rhodium, and hydridocarbonyltris (triphenylphosphine) iridium in the presence of hydrogen and carbon monoxide wherein said hydroformylation is carried in the presence of excess triphenylphosphine. This invention further discloses a process for the hydroformylation of 2-butene into 2-methylbutanal comprising reacting 2-butene with hydrogen and carbon monoxide in the presence of at least one catalyst selected from the group consisting of hydridocarbonyltris (triphenylphosphine) cobalt, hydridocarbonyltris (triphenylphosphine) rhodium, and hydridocarbonyltris (triphenylphosphine) iridium wherein said reaction is done in a reaction mixture utilizing an organic solvent in the presence of excess triphenylphosphine wherein the mole ratio of said triphenylphosphine in said reaction mixture to cobalt, rhodium, and iridium atoms in said catalyst is at least 3:1.

The critical factor in inhibiting the formation of n-pentanal in the hydroformylations of this invention is that these hydroformylations must be done in the presence of excess triphenylphosphine. It is clear that excess triphenylphosphine must somehow inhibit reaction Path C in FIG. 1, but the role that triphenylphosphine plays in doing this is unclear. In fact, it is very surprising that excess triphenylphosphine promotes the formation of a branched-chain product (2-methylbutanal) in this particular hydroformylation reaction in light of the fact that the literature indicates that excess triphenylphosphene will promote the formation of stright-chain products.

DETAILED DESCRIPTION OF THE INVENTION

In order to practice the hydroformylation process of this invention a reaction mixture comprising 2-butene, carbon monoxide, hydrogen, a catalyst, excess triphenylphosphine, and an organic solvent must be prepared. The catalysts that can be employed in the process of this invention include hydridocarbonyltris (triphenylphosphine) cobalt, hydridocarbonyltris (triphenylphosphine) rhodium, and hydridocarbonyltris (triphenylphosphine) iridium. The preferred catalyst for use in the process of this invention is $RhH(CO)(PPh_3)_3$. This rhodium system is preferred over the cobalt system and the iridium system because it produces only aldehydes in hydroformylation reactions. This is in contrast to the cobalt complex which will further reduce the aldehydes formed to alcohols. Another reason for preferring the rhodium complex is that it is catalytically active at a much lower temperature and pressure than are the cobalt and iridium complexes. The rhodium catalyst is active at 25° C. at 1 atmosphere ($1.013 \times 10^5$ pascals) pressure whereas the cobalt and iridium systems are only active at about 150° C. at 150 atmospheres ($1.52 \times 10^7$ pascals) pressure.

The solvents that can be used in the preparation of the reaction mixtures of this invention should generally be selected from organic solvents that are compatible with oxo processes. For instance, generally such a solvent should not contain double bonds which are susceptible to hydroformylation reactions. Some representative examples of suitable organic solvents include aliphatic hydrocarbons, such as normal-pentane and cyclohexane; aldehydes such as 2-methyl butanal, aromatic hydrocarbons, such as benzene, toluene and xylene (dimethylbenzene). Mixtures of the above-mentioned solvents can also be employed in the practice of this invention.

The reaction mixtures used in the process of this invention will generally contain from about 5 weight percent to about 75 weight percent 2-butene based upon the total reaction mixture. Preferably the reaction mixtures of this invention will contain from about 10 weight percent to about 50 weight percent 2-butene based upon the total reaction mixture. The amount of catalyst employed in the reaction mixtures of this invention is based on the amount of 2-butene charged into the reaction mixture. Generally, the mole ratio of 2-butene to the catalyst will range between about 500:1 and about 5000:1. The reaction mixtures of this invention must contain carbon monoxide and hydrogen. Carbon monoxide and hydrogen can be incorporated into the reaction mixtures of this invention by charging the reaction vessel containing the reaction mixture with pressurized carbon monoxide and hydrogen. If the $RhH(CO)(PPh_3)_3$ catalyst is employed only a minimal amount of pressure is required (as little as $1.013 \times 10^5$ pascals). However, if the $CoH(CO)(PPh_3)_3$ or $IrH(Co)(PPH_3)_3$ catalyst is employed then substantially more pressure will be required (about $1.0 \times 10^6$ pascals). In the case of the $RhH(CO)(PPh_3)_3$ catalyst a $H_2/CO$ pressure of $3.45 \times 10^6$ pascals to $1.38 \times 10^7$ pascals is preferred. If a $CoH(CO)(PPh_3)_3$ or $IrH(Co)(PPH_3)_3$ catalyst is employed the $H_2/CO$ pressure will preferably range between $1.5 \times 10^7$ pascals and $7.0 \times 10^7$ pascals. The $H_2/CO$ mixtures used to pressurize the reaction vessels of this invention can have widely varying ratios of $H_2$ to CO. Normally it will be desirable for the $H_2/CO$ mixtures of this invention to contain from about 10 mole percent to about 90 mole percent hydrogen and from about 10 mole percent to about 90 mole percent CO. It is generally preferred for the hydrogen-carbon monoxide mixtures of this invention to contain about 40 mole percent to 60 mole percent hydrogen and about 40 mole percent to 60 mole percent carbon monoxide. It is more preferred for the hydrogen-carbon monoxide mixtures of this invention to contain about 50 mole percent hydrogen and about 50 mole percent carbon monoxide.

The key to this invention and the critical factor in inhibiting the formation of n-pentanal is that the reaction mixtures of this invention must contain excess triphenylphosphine. In other words, the hydroformylation reactions of this invention must be carried out in the presence of excess triphenylphosphine. The hydridocarbonyltris (triphenylphosphine) cobalt, hydridocarbonyltris (triphenylphosphine) rhodium, and hydridocarbonyltris (triphenylphosphine) iridium catalyst of this invention contain triphenylphosphine molecules that are complexed into the catalysts. Three (3) moles of triphenylphosphine are complexed into the catalyst per mole of cobalt, rhodium, or iridium. Thus, excess triphenylphosphine is the amount of triphenylphosphine in the reaction mixture that is in excess of the amount which is complexed into the catalyst. The molar amount of excess triphenylphosphine is therefore the number of moles of triphenylphosphine in excess of 3 times the number of moles of cobalt, rhodium and iridium atoms in the reaction mixture. Thus, in order to practice the process of this invention the ratio of triphenylphosphine molecules to cobalt, rhodium, and iridium atoms in the reaction mixture must be at least 3:1. For example, if there is one mole of cobalt in the catalyst employed in the reaction mixture and five moles of triphenylphosphine then there are 2 moles of excess triphenylphosphine (5 moles total − 3 moles complexed with catalyst = 2 moles excess) and the ratio of triphenylphosphine to cobalt is 5:1. Normally, the mole ratio of triphenylphosphine molecules to the transition metal used in the catalyst will range between 3:1 and 400:1. It should be noted that the number of moles of transition metals in the catalyst employed in a reaction mixture will be equal to the number of moles of catalyst in the reaction mixture since there is one transition metal atom per catalyst complex. It is generally preferred for the ratio of triphenylphosphine molecules to cobalt, rhodium and iridium atoms in the reaction mixture to range from about 6:1 to about 100:1. It is more preferred for the ratio between the triphenylphosphine molecules in the reaction mixture and the transition metal in the catalyst employed to range from 9:1 to 40:1.

Since it is important for the 2-butene, carbon monoxide, hydrogen, catalysts, and triphenylphosphine to be distributed somewhat uniformly throughout the organic solvent employed in the reaction mixture, it is desirable for the reaction mixture to be agitated during the hydroformylation reaction. The hydroformylation process of this invention can be effectuated at any temperature ranging from about 25° C. to about 200° C., if the $RhH(CO)(PPh_3)_3$ catalyst is employed. If the $CoH(CO)(PPh_3)_3$ or $IrH(Co)(PPH_3)_3$ catalyst is employed a temperature of about 150° C. to about 220° C. will be required in order to carry out the hydroformylation of this invention. If the $RhH(CO)(PPh_3)_3$ is employed it will generally be preferred for the temperature utilized to range between 50° C. and 150° C. Using the rhodium catalyst it is more preferred for the temperature utilized to be from 90° C. to 130° C.

The optimum reaction time for the hydroformylation process of this invention will vary with the catalyst utilized, the catalyst concentration, the 2-butene concentration, the $H_2/CO$ pressure, and the reaction temperature. However, the reaction time employed normally will be between 15 minutes and 10 hours. The reaction time will preferably range between 30 minutes and 4 hours with the most preferred reaction time generally ranging from 1 to 2 hours.

The catalytic cycle for the hydroformylation of 2-butene utilizing a triphenylphosphine rhodium complex catalyst is illustrated below as FIG. 2.

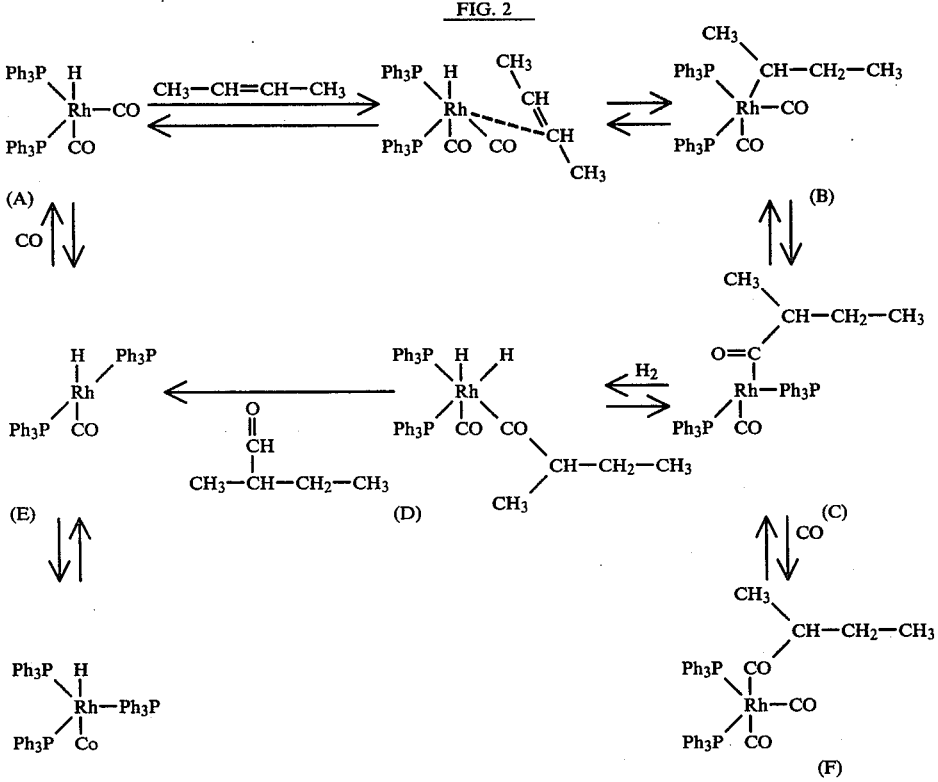

FIG. 2

It should be noted that the exact conformations of the rhodium complexes illustrated are not known with certainty. In this proposed reaction cycle the initial step is associative attack of the 2-butene on the species RhH(Co)$_2$(Ph$_3$P)$_2$, which is shown as (A) in the illustration, which thus results in the formation of complex (B). The latter then undergoes CO insertion to form (C) which subsequently undergoes oxidative addition of molecular hydrogen to give complex (D). The last of these steps, which is the only one in the cycle that involves a change in the oxidation state of the rhodium, is probably rate-determining. The final steps are another H transfer to the carbon atom of the acyl group in (D), followed by loss of 2-methylbutanal and regeneration of the four-coordinate species (E).

The following examples are included to further illustrate the process of this invention and to compare it with other hydroformylations outside of its scope. Such comparisons clearly show the unexpected result achieved by carrying out the hydroformylation process of this invention in the presence of excess triphenylphosphine. The following examples are merely for the purpose of illustration and are not to be regarded as limiting the scope of the invention or the manner in which it can be practiced. Unless specifically indicated otherwise, parts and percentages are given by weight.

EXAMPLE 1

10 grams of 2-butene (0.18 moles) was dissolved in 150 ml (milliliters) of meta-xylene. Then 0.165 grams (0.18 millimoles) of RhH(CO)(PPH$_3$)$_3$ and 0.14 grams (0.54 millimoles) of triphenylphosphine was added to the mixture. After the catalyst and triphenylphosphine had dissolved the mixture was charged into a 300 milliliter autoclave under argon. The temperature of the autoclave was raised to 100° C. with a mixture of 50 percent hydrogen and 50 percent carbon monoxide being used to pressurize the autoclave to 1050 pounds per square inch gauge (7.34×10$^6$ pascals). The H$_2$/CO mixture was recharged as consumed to maintain a pressure of at least 1000 pounds per square inch gauge (7.0×10$^6$ pascals). After about 88 minutes VPC (vapor phase chromatograph) analysis indicated a 90 percent conversion of 2-butene to 2-methylbutanal and n-pentanal. This analysis further indicated that this hydroformylation technique produced 95 percent 2-methylbutanal and 5 percent n-pentanal.

EXAMPLE 2

The same procedure that was specified in Example 1 was employed in this experiment except that 1 gram (3.8 millimoles) of triphenylphosphine was added to the reaction mixture. After 274 minutes the conversion of 2-butenes into 2-methylbutanal and normal-butanal was determined by VPC analysis to be about 89 percent. This VPC analysis also revealed that the mixture produced contained 97 percent 2-methylbutanal and 3 percent n-pentanal.

EXAMPLE 3

The procedure specified in Example 2 was repeated in this experiment except that the hydroformylation temperature employed was 125° C. After 110 minutes, VPC analysis indicated a conversion of about 94 percent with a selectivity for 2-methylbutanal of 92.5 percent (with the mixture formed containing 7.5 percent n-pentanal).

EXAMPLE 4

The procedure procedure specified in Example 1 was repeated except that 17.6 grams (76 millimoles) of triphenylphosphine was added to the reaction mixture. After 375 minutes, VPC analysis indicated a conversion of 32 percent. This hydroformylation produced 95 percent 2-methylbutanal and 5 percent n-pentanal.

COMPARATIVE EXAMPLE 5

The procedure specified in Example 1 was repeated in this experiment except that no excess triphenylphosphine was added to the reaction mixture. After 27 minutes, VPC analysis indicated a 97 percent conversion. The mixture produced contained about 72 percent 2-methylbutanal and 28 percent n-pentanal.

By comparing this experiment with Example 1 the dramatic effect that excess triphenylphosphine has in inhibiting the formation of n-pentanal is clearly shown. An even more dramatic difference in the amount of n-pentanal formed can be seen by comparing this example with Example 2. By practicing the process of this invention, carrying out the hydroformylation in the presence of excess triphenylphosphine, the amount of n-pentanal produced can be reduced almost ten fold.

While certain representative embodiments and details have been shown for the purpose of illustrating this invention, it will be apparent to those skilled in the art that various changes and modifications can be made therein without departing from the scope of this invention.

What is claimed is:

1. A process for the hydroformulation of 2-butene into 2-methylbutanal comprising: reacting 2-butene with hydrogen and carbon monoxide in the presence of a hydridocarbonyltris (triphenylphosphine) rhodium catalyst at a temperature of from 25° C. to 200° C. and a pressure of at least 1.013×10$^5$ pascals for a reaction time of between 15 minutes and 10 hours wherein said reaction is done in a reaction mixture utilizing an organic solvent in the presence of excess triphenylphosphine wherein the mole ratio of triphenylphosphine in said reaction mixture to rhodium atoms in said catalyst is between 3:1 and 400:1.

2. A process as specified in claim 1 wherein the mole ratio of said triphenylphosphine present to said catalyst is between 6:1 and 100:1.

3. A process as specified in claim 2 wherein the mole ratio of said triphenylphosphine present to said catalyst is between 9:1 and 40:1.

4. A process as specified in claim 3 wherein said hydroformylation is carried out at a temperature ranging from 50° C. to 150° C.

5. A process as specified in claim 4 wherein said hydroformylation is carried out at a temperature ranging from 90° C. to 130° C.

6. A process as specified in claim 5 wherein said hydroformylation is carried out at a pressure of 3.45×10$^6$ to 1.38×10$^7$ pascals.

* * * * *